United States Patent

Jones

Patent Number: 6,153,889
Date of Patent: Nov. 28, 2000

[54] METHOD AND AN APPARATUS FOR INSPECTING ARTICLES

[75] Inventor: Alan R. Jones, Derby, United Kingdom

[73] Assignee: Rolls-Royce plc, London, United Kingdom

[21] Appl. No.: 09/266,817

[22] Filed: Mar. 12, 1999

[30] Foreign Application Priority Data

Mar. 20, 1998 [GB] United Kingdom ................... 9805861

[51] Int. Cl.[7] .................................................. G01N 21/88
[52] U.S. Cl. .............................. 250/559.45; 250/559.46; 416/96 R; 416/97 R
[58] Field of Search ........................... 250/559.4, 559.44, 250/559.45, 559.46; 416/96 R, 97 R, 97 A

[56] References Cited

U.S. PATENT DOCUMENTS

| | | |
|---|---|---|
| 3,566,669 | 3/1971 | Lawrence . |
| 3,700,903 | 10/1972 | Adler et al. .............................. 250/217 |
| 5,111,046 | 5/1992 | Bantel . |
| 5,246,340 | 9/1993 | Winstanley et al. ................... 416/97 R |
| 5,625,196 | 4/1997 | Williams .............................. 250/559.45 |

FOREIGN PATENT DOCUMENTS

| | | |
|---|---|---|
| 2164746A | 3/1986 | United Kingdom . |
| 2283538A | 5/1995 | United Kingdom . |

*Primary Examiner*—Huy Mai
*Attorney, Agent, or Firm*—W. Warren Taltavull; Farkas & Manelli PLLC

[57] ABSTRACT

An apparatus (42) for inspecting an as cast turbine blade (40), with impingement cooling passages (36) (see FIG. 2), comprises a vacuum pump (52) arranged to evacuate the interior of the turbine blade (40) through pipe (48) and valve (54) and a supply of steam (46) arranged to supply steam to the interior of the turbine blade (40) through the pipe (48) and a valve (50). An infrared camera (56) is arranged to view the outer surface (32) of the turbine blade (40) to detect hot spots produced on the outer surface (32) of the turbine blade (40) by jets of steam impinging on the inner surface (35) of the turbine blade (40) from the cooling passages (36). A processor (60) records the images produced by the camera (56) and analyses the images to determine if the cooling passages (36) have been formed and if they have been formed in the correct position.

46 Claims, 4 Drawing Sheets

METHOD AND AN APPARATUS FOR INSPECTING ARTICLES

The present invention relates generally to a method and an apparatus for inspecting articles. The invention is particularly suitable for inspecting impingement cooling passages, or film cooling passages, of hollow turbine blades or hollow turbine vanes of gas turbine engines to determine whether such cooling passages are blocked or if they are in an incorrect position. The invention is also suitable for inspecting articles to determine whether there are cracks, debonds, voids, delaminations, oxidation or corrosion in the article and also if there is insufficient adhesion between the article and a coating on the article.

The turbine blades and turbine vanes of gas turbine engines usually comprise cooling passages for single or multi pass convection cooling, impingement cooling or film cooling purposes. The film cooling passages extend through the wall of the turbine blade from a first, interior, surface to a second, exterior, surface of the turbine blade. The impingement cooling passages extend through structure within the turbine blade and are spaced from the first, interior, surface of the turbine blade. The convection cooling passages generally extend longitudinally in the wall of the turbine blade. Other cooling passages extend through structure within the turbine blade. The turbine blades and turbine vanes may comprise various combinations of any one or ore of convection cooling passages, impingement cooling passages and film cooling passages.

These turbine blades and turbine vanes are cast using the investment casting technique in which ceramic: cores, located in ceramic shell moulds, are used to define the impingement cooling passages and other cooling passages within the structure of the turbine blade. The film cooling passages are generally formed by machining through the walls of the turbine blades to connect with other cooling passages within the structure of the turbine blade.

However, there is a requirement to inspect the turbine blades and turbine vanes to ensure that the impingement and/or other and/or film cooling passages have been formed without blockages and/or that the cooling passages have been formed in the correct position. The blockages in the impingement and other cooling passages may be formed because not all of the ceramic cores have been removed, or the ceramic cores may have cracked during casting to allow metal to block the cooling passage and the impingement and other cooling passages may have been formed in the wrong position because the cores moved within the ceramic shell mould. Blockages in the film cooling passages may be formed by incorrect machining etc.

If one or more of the other cooling passages has been displaced from its nominal position, a subsequently formed film cooling passage interconnecting with the other cooling passage may only graze or even miss the other cooling passage, it may interconnect at the wrong position or the tool, may pass across the other cooling passage and damage the opposite wall of the other cooling passage. These effects may reduce the strength of the turbine blade and are difficult to detect. Thus it is desirable to detect any discrepancies in the impingement and/or other cooling passages before the film cooling passages are formed by expensive machining processes.

It is known to use borescopes to inspect the interior of cast turbine blades and turbine vanes to ensure that the cooling passages have been correctly formed. However, the use of borescopes is a time consuming and labour intensive process. Furthermore it has the disadvantage of not being able to detect some specific forms of blockage unless specific lighting techniques or light guides are used.

It is known to use X-ray computer tomography to inspect articles and this would be possible for cast turbine blades and turbine vanes to ensure that the cooling passages have been correctly formed. However, X-ray computer tomography equipment is very expensive and the cost of generating tomographs of a large number of sections from each turbine blade or turbine vane would make the process uneconomical. Furthermore it not possible to detect all the cooling passages in some portions of the turbine blade or turbine vane and there is a lower limit to the size of feature that can be resolved by X-ray computer tomography and some blockages may be to thin to be detected.

It is also known to use thermography to inspect, turbine blades to determine if the cooling passages are blocked.

U.S. Pat. No. 3,566,669 passes a hot gas through and out of the cooling passages of a turbine blade and through and out of a reference passage having different wall thicknesses. An infrared camera views the external surface of the turbine blade and the reference passage to determine if the cooling passages are at the correct position relative to the outer surface of the wall and/or to determine if any of the cooling passages are blocked.

UK patent GB2164746B passes a hot gas through the film cooling passages of a turbine blade. An infrared camera views the film cooling passages and determines the relative intensities of the black body radiation emitted by the film cooling passages to determine if any of the film cooling passages are blocked.

U.S. Pat. No. 5,111,046 is similar to GB2164746B but subsequently passes a cold gas through the film cooling passages of the turbine blade to determine the presence of certain type of blockage.

These patents do not disclose how to detect blockages in cooling passages if the hot gas cannot exit the turbine blade through film cooling passages. Also any hot gas passing into the cooling passages in the turbine blade, as used in the above patents, may not produce effective heat transfer in the areas of the turbine blade to be inspected and thus the inspection technique is not sensitive enough to determine any blockages in impingement cooling passages or other cooling passages.

Accordingly the present invention seeks to provide a method of inspecting an article which reduces the above mentioned problems.

Accordingly the present invention provides a method of inspecting an article, the article having a first surface and a second surface facing in the opposite direction to the first surface, comprising the steps of:
(a) forming an enclosed volume at least partially defined by the first surface of the article,
(b) removing air from the enclosed volume,
(c) supplying a condensable heating fluid to the enclosed volume,
(d) directing a flow of the condensable heating fluid onto or over the first surface of the article to cause the temperature of the first surface to change,
(e) viewing the second surface of the article during the temperature change to produce a series of images, and
(f) analysing the series of images to determine the presence or absence of defects in the article.

Preferably the method comprises injecting a small quantity of the condensable heating fluid into the enclosed volume after step (a) and before step (b).

Alternatively the method may comprise injecting a small quantity of the condensed heating fluid into the enclosed volume after step (a) and before step (b).

Preferably step (c) comprises supplying steam to the enclosed volume.

Step (e) may comprises applying a thermochromic material to the second surface of the article and viewing the second surface of the article with a camera sensitive to radiation in the visible light band. Step (e) may comprise viewing the second surface of the article with a video camera, a cine camera or a CCD camera.

Preferably step (e) comprises viewing the second surface of the article with a camera sensitive to radiation in the infra red band.

A calibrated emissivity coating may be applied to the second surface of the article.

Preferably step (d) comprises directing a plurality of jets of the condensable heating fluid onto the first surface of the article.

Preferably step (a) comprises forming the enclosed volume solely by the first surface of the article.

Preferably step (d) comprises directing a plurality of jets of the condensable heating fluid through passages in the article onto the first surface of the article.

Preferably step (b) comprises evacuating the enclosed volume.

Preferably the article is a turbine blade or a turbine vane.

Alternatively step (a) may comprise forming the enclosed volume partially with a vessel.

Step (d) may comprises supplying a plurality of jets of the condensable heating fluid through passages in the vessel onto the first surface of the article.

The article may be a composite material article, a laminated material article or a coated article.

The present invention also provides a method of inspecting an article, the article having a plurality of passages extending from a first surface to a second surface facing in the opposite direction to the first surface, comprising the steps of:

(a) forming an enclosed volume at least partially defined by the second surface of the article and a first surface of a vessel, (b) removing air from the enclosed volume, (c) supplying a condensable heating fluid to the enclosed volume, (d) directing a flow of the condensable heating fluid through the passages onto the first surface of the vessel to cause the temperature of the first surface of the vessel to change, (e) viewing the second surface of the vessel during the temperature change to produce a series of images, and (f) analysing the series of images to determine the presence or absence of defects in the article.

Preferably the method comprises injecting a small quantity of the condensable heating fluid into the enclosed volume after step (a) and before step (b).

Alternatively the method comprises injecting a small quantity of the condensed heating fluid into the enclosed volume after step (a) and before step (b).

Preferably step (c) comprises supplying steam to the enclosed volume.

Step (e) may comprise applying a thermochromic material to the second surface of the article and viewing the second surface of the vessel with a camera sensitive to radiation in the visible light band. Preferably step (e) comprises viewing the second surface of the vessel with a video camera, a cine camera or a CCD camera.

Preferably step (e) may comprise viewing the second surface of the vessel with a camera sensitive to radiation in the infra red band.

A calibrated emissivity coating may be applied to the second surface of the vessel.

Preferably step (d) comprises directing a plurality of jets of the condensable heating fluid onto the first surface of the vessel.

Preferably step (d) comprises directing a plurality of jets of the condensable heating fluid through passages in the article onto the first surface of the vessel.

Preferably step (b) comprises evacuating the enclosed volume.

Preferably the article is a turbine blade or a turbine vane.

The present invention also provides an apparatus for inspecting an article, the article having a first surface and a second surface facing in the opposite direction to the first surface, the first surface at least partially defining an enclosed volume, comprising means to remove air from the enclosed volume, means to supply a condensable heating fluid to the enclosed volume, means to direct a flow of the condensable heating fluid onto or over the first surface of the article to cause the temperature of the first surface to change, means to view the second surface of the article during the temperature change to produce a series of images, and means to analyse the series of images to determine the presence or absence of defects in the article.

The present invention also provides an apparatus for inspecting an article, the article having a plurality of passages extending from a first surface to a second surface facing in the opposite direction to the first surface, comprising a vessel having a first surface to define an enclosed volume with the second surface of the article, means to remove air from the enclosed volume, means to supply a condensable heating fluid to the enclosed volume, means to direct a flow of the condensable heating fluid onto or over the first surface of the vessel to cause the temperature of the first surface to change, means to view the second surface of the article during the temperature change to produce a series of images, and means to analyse the series of images to determine the presence or absence of defects in the article.

Preferably there are means to inject a small quantity of the condensed heating fluid into the enclosed volume.

Preferably the means to supply a condensable heating fluid comprises a supply of steam.

The second surface of the article, or the second surface of the vessel, may have a thermochromic material. The means to view the second surface of the article, or the second surface of the vessel, may comprise a camera sensitive to radiation in the visible light band. The means to view the second surface of the article, or the second surface of the vessel, may comprise a video camera, a cine camera or a CCD camera.

Preferably the means to view the second surface of the article, or the second surface of the vessel, comprises a camera sensitive to radiation in the infra red band.

The second surface of the article, or second surface of the vessel, may have a calibrated emissivity coating.

Preferably the enclosed volume is defined solely by the first surface of the article.

Preferably the article comprises a plurality of passages to direct a plurality of jets of the condensable heating fluid onto the first surface of the article.

Alternatively the article may comprise a plurality of passages to direct a plurality of jets of the condensable heating fluid onto the first surface of the vessel.

Preferably the article is a turbine blade or a turbine vane.

Alternatively the enclosed volume is defined by the first surface of the article and a first surface of a vessel.

The vessel may comprise a plurality of passages to direct a plurality of jets of the condensable heating fluid onto the first surface of the article.

Preferably the means to remove gas from the enclosed volume comprises means to evacuate the enclosed volume.

The article may be a composite material article, a laminated material article or a coated article.

The present invention will be more fully described by way of example with reference to the accompanying drawing, in which.

Figure 1:
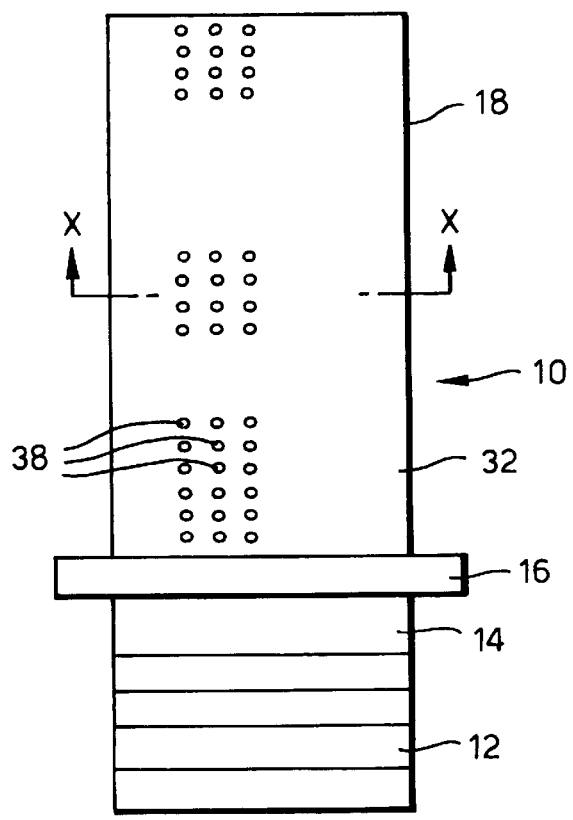
FIG. 1 is a view of a gas turbine blade.
Figure 2:
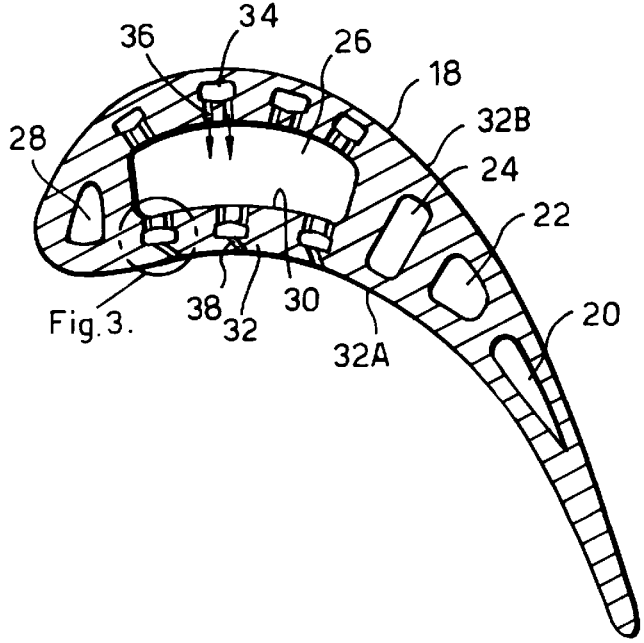
FIG. 2 is an enlarged cross-sectional view in the direction of arrows A—A through the gas turbine blade shown in FIG. 1.
Figure 3:
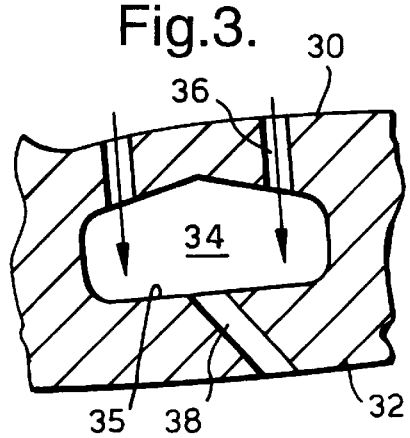
FIG. 3 is a further enlarged portion of part of FIG. 2.

A turbine blade 10, as shown in FIGS. 1 to 3, comprises a root portion 12, a shank portion 14, a platform portion 16 and an aerofoil portion 18. The turbine blade 10 is suitable for use in a gas turbine engine (not shown). The aerofoil portion 18 has a number of lengthwise extending chambers 20, 22, 24, 26 and 28. The chamber 20 is adjacent the trailing edge of the aerofoil portion 18 and the chamber 30 is adjacent the leading edge of the aerofoil portion 18. The aerofoil portion 18 of the turbine blade 10 has a first, inner, surface 30 and a second, outer, surface 32. The inner surface 30 defines the chamber 26. The second surface 32 has a pressure surface 32A and a suction surface 32B.

The chamber 26 is the main chamber and there are a plurality of further chambers 34 which are narrow relative to the main chamber 26 which surround the main chamber 26 and which are positioned between the first surface 30 and the second surface 32. The chambers 34 also extend lengthwise of the aerofoil portion 18. Each of the chambers 34 is interconnected with the main chamber 26 by one or more cooling passages 36. The chambers 34 between the chamber 26 and the pressure surface 32A are interconnected to the pressure surface 32A by one or more film cooling passages 38. The chambers 34 have first, inner, surfaces 35 adjacent the second, outer, surface 32 of the aerofoil portion 38. A more complete description of the turbine blade is present in UK patent GB2283538B.

In operation, cooling air is forced up the chambers 34 adjacent the suction surface 32B of the aerofoil portion 18 from the root portion 12. The cooling air then flows through the cooling passages 36 into and across the main chamber 26. The cooling air then flows from the main chamber 2E through the cooling passages 36 into the chambers 34 adjacent the pressure surface 32A. The cooling air flowing through the cooling passages 36 impinges upon the first surfaces 35 of the chamber 34 to provide impingement cooling of the wall of the aerofoil portion 18. The cooling air then flows through the film cooling passages 38 to exit the aerofoil portion 18 and to provide a cooling film of air on the pressure surface 32A of the aerofoil portion 18.

As discussed earlier the turbine blades 10 are generally manufactured by investment casting using ceramic shell moulds and ceramic cores to define the chambers 20, 22, 24, 26 and 28, the further chambers 34 and the passages 36. After the metal has been cast in the ceramic shell mould the ceramic shell mould and ceramic cores are removed. The passages 38 are generally produced by electrochemical machining, electodischarge machining or laser machining etc.

It is desirable to inspect the as cast turbine blade, or turbine vane, before the film cooling passages 38 are formed, to ensure that the chambers 34 and passages 36 have been formed and/or that they are in the correct position.

Figure 4:
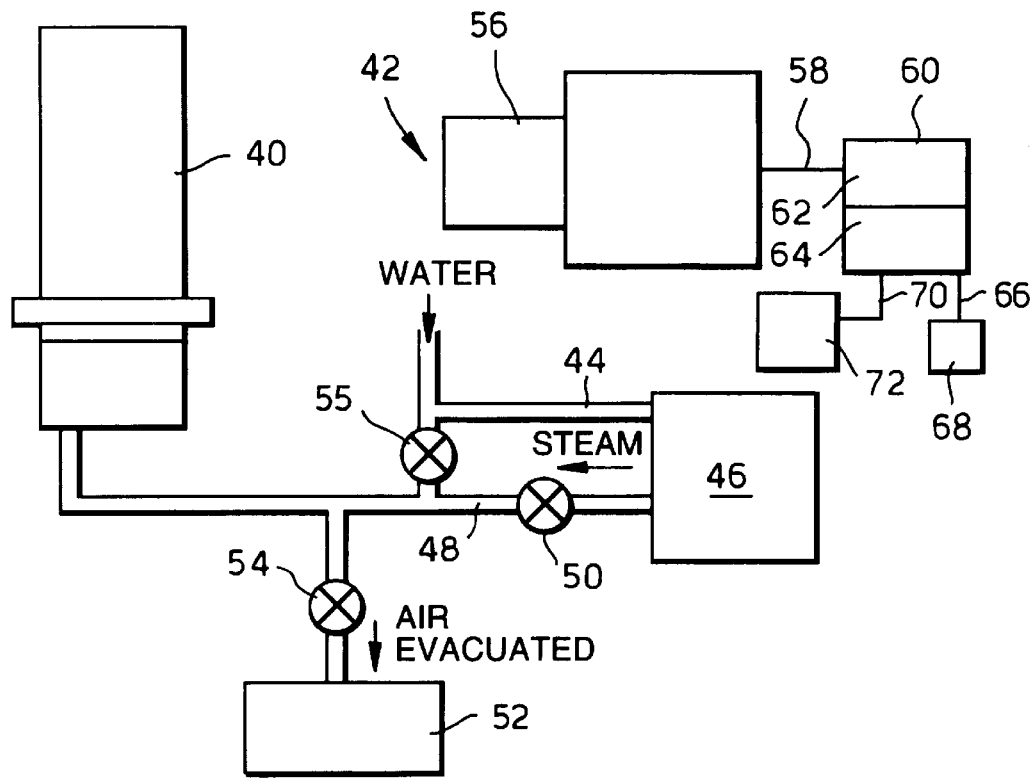
FIG. 4 is an apparatus for inspecting an article according to the present invention.

An apparatus 42 for inspecting the as cast turbine blades 40, or turbine vanes, is shown in FIGS. 4. the apparatus 42 comprises a supply of steam 46, for example boiler, which is supplied with water via a pipe 44. The supply of steam 46 is interconnected to the main chamber 26 in the aerofoil portion 18 of the as cast turbine blade 40 via a pipe 48. The pipe 48 has a valve 50 to control the supply of steam along the pipe 48 to the chamber 26. The pipe 44 is also interconnected to the chamber 26 via the pipe 48 and the pipe 48 has a valve 55 to control the supply of water along the pipe 48 to the chamber 26. A vacuum pump 52 is also interconnected to the main chamber 26 in the aerofoil portion 18 of the as cast turbine blade 40 via the pipe 48. A valve 54 is provided to control the removal of gas from the chamber 26.

A camera 56 is provided to view the second, outer, surface 32 of the aerofoil portion 18 of the as cast turbine blade 40. The camera 56 supplies electrical image signals along line 58 to a processor 60, which comprises an image recorder 62 and an image analyser 64. The processor 60 supplies electrical signals along line 66 to an indicator 68 and/or along line 70 to a display 72. The processor 60 may comprise a personal computer or other computer. The indicator 68 may for example comprise a lamp which Lights to indicate that the passages 36 in the as cast turbine blade 40 are present and are in the correct position. The display 72 may be a television screen, or monitor to show the images of the as cast turbine blade 40 to an operator.

The camera 56 is preferably a camera sensitive to radiation in the infrared band, but the camera 56 may be a camera sensitive to radiation in the visible band if the turbine blade 40 is coated with a thermochromic material, for example a paint, or coating, which contains thermochromic liquid crystals or a self adhesive tape having thermochromic liquid crystals. The camera may be a thermal imaging camera, a video camera, a cine camera or a CCD camera.

In order to inspect the as cast turbine blade 40 the pipe 48 is fitted and sealed to the portion of the chamber 26 in the root portion 12 of the turbine blade 40. Initially all of the valves 54, 55 and 56 are closed. The turbine blade 40 and camera 56 are so arranged to enable one surface of the turbine blade 40 to be viewed by the camera 56, in particular the turbine blade 40 may be mounted in a fixture (not shown).

When the turbine blade 40 is connected to the pipe 48 and the chamber 26 is sealed, the valve 54 is opened to allow the vacuum pump to evacuate the chamber 26 and hence the chambers 34 and cooling passages 36, assuming the chambers 34 and cooling passages 36 have been correctly formed. After the chamber 26 has been evacuated the valve 54 is closed and the valve 50 is opened to allow steam to be supplied to the chamber 26. As the steam is admitted to the chamber 26 the temperature of the second surface 32 of the turbine blade 40 is viewed by the camera 56 and recorded by the image recorder 62 of the processor 60. The analyser 64 of the processor 60 analyses the images of the stored in the image recorder 62 to determine whether the turbine blade 40 is satisfactory or not.

In the turbine blade 40 the steam flows through the chamber 26 and some of the steam flows through the cooling passages 36 and the steam impinges on the first surfaces 35 of the chambers 34, in the form of discrete jets. The first surfaces 35 of the chambers 34 are those adjacent the second surface 32 of the aerofoil portion 18 of the turbine blade 40. Each jet of steam creates a very localised condensing heat transfer to the wall of the turbine blade 40 which in turn generates a thermal wave that passes through the thickness of the wall. Each thermal wave creates a transient hot spot on the second surface 32 of the aerofoil portion 18 of the turbine blade 40, the region around each transient hot spot heats up more slowly to the same temperature as the transient hot spot.

The camera 56 is arranged to view the second surface 32 of the aerofoil portion 18 of the turbine blade 40 to detect the transient hot spots on the surface 32 of the aerofoil portion 18 of the turbine blade 40. Thus the presence of transient hot spots at the appropriate positions in the images of the aerofoil portion 18 of the turbine blade 40 indicates that the cooling passages 36 have been correctly formed.

On the other hand the lack of transient hot spots at the appropriate positions, or transient hot spots at unexpected positions, in the images of the aerofoil portion 18 of the turbine blade 40 indicates that the cooling passages 36 have been incorrectly formed. The turbine blades 40 with incorrectly formed cooling passages 36 may be discarded before any more expensive machining processes are performed.

The processor 60 sends appropriate signals to the display 68 to show whether a particular turbine blade 40 has correctly or incorrectly formed cooling passages 36. If the thermal diffusivity of the material of the turbine blade 40 is known a time:temperature history of a transient hot spot enables the processor 60 to determine the local wall thickness of the aerofoil 18, or if the thickness is known the thermal diffusivity may be calculated.

The use of steam to heat the turbine blade 40 is advantageous because it provides the condensing heat transfer to the turbine blade 40. The condensation of the steam in the chambers 34, when the steam from the cooling passages 36 contacts the wall, allows more steam to be drawn into the chambers 34 from the chamber 26 to create impingement jets of steam which produce significant flow of heat into the wall of the aerofoil portion 18. These impingement jets of steam occur until the pressure ratio across the cooling passages 36 falls below a critical value. The critical value depend upon the geometry of the chamber 34 and the cooling passage 36. The pressure ratio may fall due to a decrease in pressure in chamber 26 or an increase in pressure in chamber 34.

In order to aid the removal of gas, or air, from the chamber 26 the above method may be modified by firstly opening the valve 50 to allow a small quantity of steam into the chamber 26 which will condense on the walls of the chambers 26 and 34 to form a film of water. The valve 50 is then closed and valve 54 is opened to evacuate the chambers 26 and 34. The film of water in the chambers 26 and 34 evaporates at low pressure displacing the gas, or air, during the evacuation process. Air is a non-condensable gas., which inhibits the flow of the impingement jets of steam onto the surface of the wall, and may reduce the rate of heat transfer. The small quantity of steam also heats up the root portion 12 and the shank portion 14 of the turbine blade 10 through which the steam has to flow to reach the chambers 34 and cooling passages 36. The heating up of the root, portion 12 and shank portion 14 by the steam reduces the amount of condensation occurring in the chambers 34 and cooling passages 36.

Alternatively to aid the removal of gas, or air, from the chamber 26 the above method may be modified by firstly opening the valve 55 to allow a small quantity of water into the chamber 26. The valve 55 is then closed and valve 54 is opened to evacuate the chambers 26 and 34. The water in the chambers 26 and 34 evaporates at low pressure displacing the gas, or air, during the evacuation process. An advantage of using water is that it does not heat the turbine blade and so does not reduce the achievable amplitude of the temperature step that can be created.

It is also possible to preheat the root portion 12 and the shank portion 14 of the turbine blade 10 in an oven to approximately 90° C.

Following preheating of the root portion 12 and shank portion 14 of the turbine blade 10, the aerofoil portion 18 is cooled, for example by a flow of cool gas, to enable transient hot spots with a large temperature difference from the surrounding regions to be produced. The cooling is performed quickly to minimise the possibility of cooling the root portion 12 and the shank portion 14 of the turbine blade 10.

Figure 9:
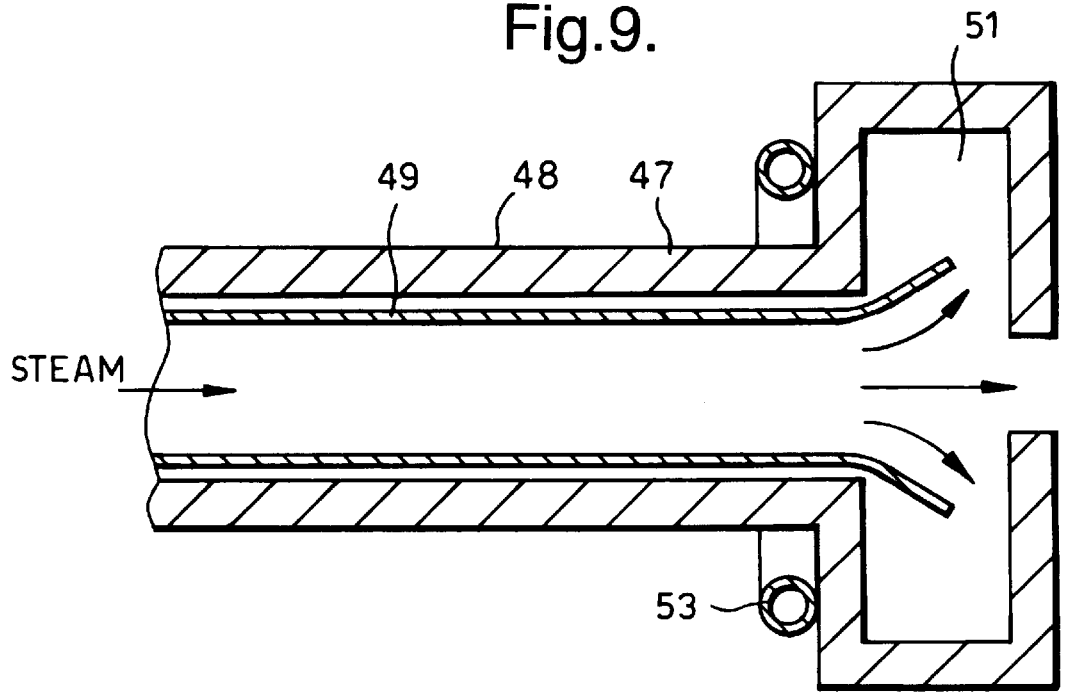
FIG. 9 is a cross-sectional view through a pipe shown in FIG. 4.

The pipe 48, as shown more clearly in FIG. 9, preferably comprises a thick outer wall 47 to contain the steam pressure and a thin inner wall 49 of low thermal mass and low thermal conductivity to separate the flow of steam from the thick outer wall 47, which is at ambient, room, temperature. The thin inner wall 49 quickly heats up when steam flows through the pipe 48 so minimising the amount of condensation which is drawn into turbine blade 10. The pipe 48 includes a steam trap chamber 51 to prevent condensate, which has formed on the thick outer wall 47, from entering the chamber 26 of the turbine blade 40. The steam flowing through the inner pipe 49 flows radially outwardly into the chamber 51 to prevent condensate on the outer pipe 47 flowing into the turbine blade 40. A further steam pipe 53, or other heating apparatus, is positioned in proximity to the chamber 51 and pipe 48 to minimise condensation of steam.

The turbine blade may be coated with an emissivity coating to assist the resolution of transient hot spots or to provide a calibrated emissivity surface to allow accurate measurement of the temperature to be made.

The advantage of the present invention is that it allows the cooling passages 36 of the turbine blade 40 to perform their required function, but under different circumstances. The present invention also allows the turbine blades be inspected more quickly than using a borescope or X-ray computer tomography. The present invention uses evacuation and condensation heating to create a very high rate of temperature increase on the inside of the turbine blade unlike conventional thermography which uses hot gases which have a very low rate of temperature increase. The advantage of the very high rate of temperature increase is that it makes it possible to resolve smaller features, i.e. the impingement cooling holes. The present invention does not require a flow of the steam through and out of the turbine blade unlike conventional thermography, enabling the turbine blade to be inspected before all their cooling passages have been formed and thus enables defective turbine blades to be rejected before being subjected to expensive machining processes. It is also possible to determine the distance of hot spots from datum features on the turbine blades for each individual turbine blade. This information may be used in subsequent machining processes to guide the machining process to eliminate the problem of machining film cooling holes in turbine blades in a position which is incompatible with the actual position of the internal cooling passages, thus saving on scrap and eliminating the need for further inspection.

The use of thermochromic liquid crystals and a video camera sensitive to radiation in the visible band is particularly suitable for low volumes of turbine blades, and an inspector may view each image of a recording made by the video camera, this avoids the expense of a thermal imaging camera.

The use of thermochromic liquid crystals and a CCD camera sensitive to radiation in the visible band is particularly suitable for moderate volumes of turbine blades and qualitative inspection only is required, a processor is preferred to analyse the images made by the CCD camera.

The use of a camera sensitive to radiation in the infrared band is particularly suitable for high volumes of turbine blades, to eliminate the expense of the thermochromic liquid crystals. To improve resolution a non-calibrated emissivity coating may be applied to the turbine blades. If quantitative information is required a calibrated emissivity coating is applied to the turbine blades.

Figure 5:
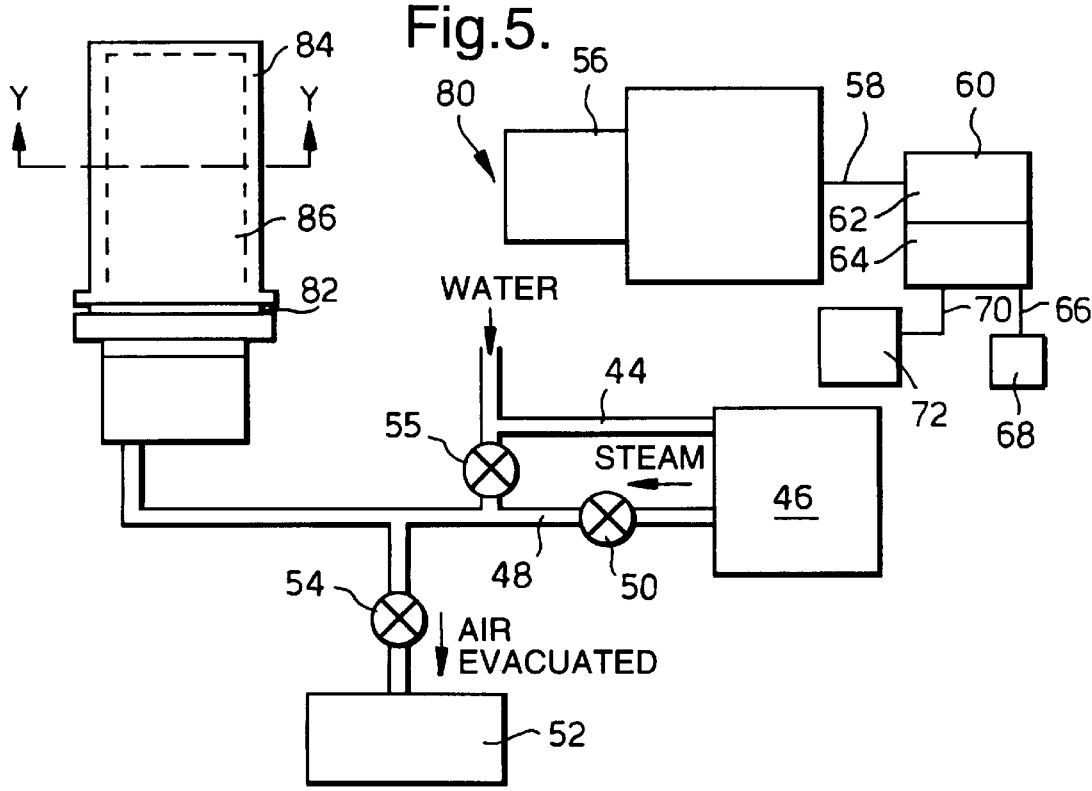
FIG. 5 is another apparatus for inspecting an article according to the present invention.
Figure 6:
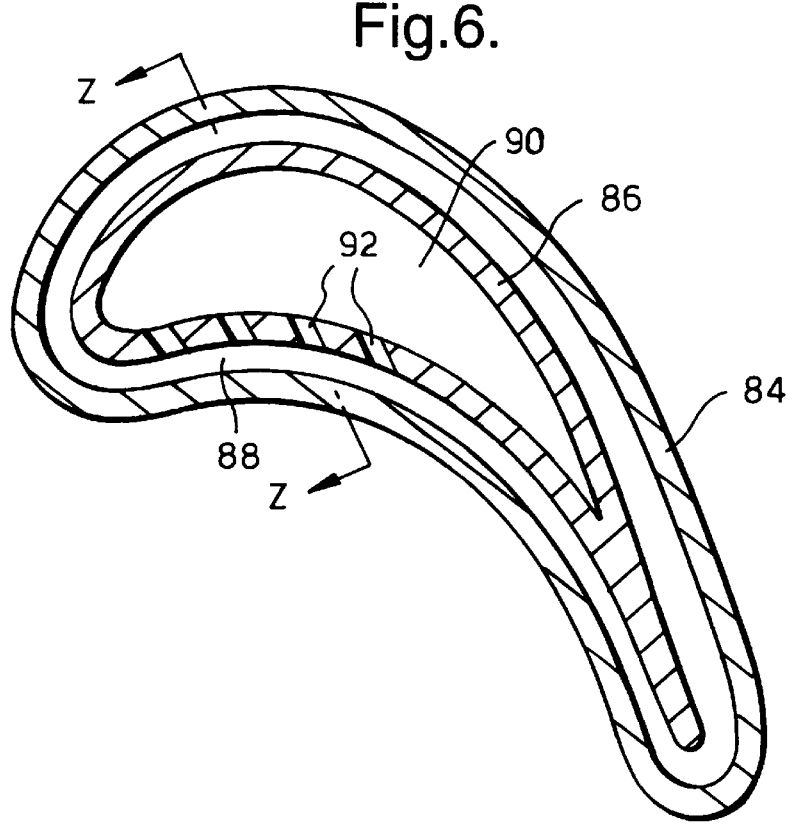
FIG. 6 is a enlarged cross-sectional view through the article and part of the apparatus in the direction of arrows Y—Y in FIG. 5.
Figure 7:
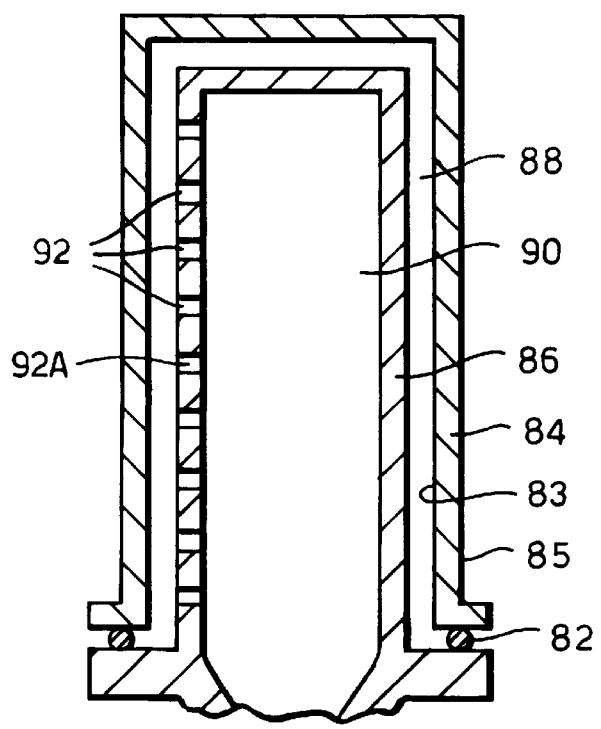
FIG. 7 is a cross-sectional view in the direction of arrows Z—Z in FIG. 6.

An apparatus 82 for inspecting turbine blades 86 is shown in FIG. 5, 6 and 7. The apparatus 82 is substantially the same as the apparatus 42 but differ because the turbine blades 86 have film cooling passages 92 extending through the wall of the turbine blades 86 from chamber 90.

The apparatus 80 differs in that a vessel 84, having an aerofoil shape in cross-section, is placed over the aerofoil portion of the turbine blade 86. The vessel 84 is spaced from the wall of the turbine blade 86 by a uniform clearance 88 to define an enclosed volume between the vessel 84 and the wall of the turbine blade 86. The open end of the vessel 84 is sealed to the platform portion of the turbine blade 86 by a seal strip 82. The pipe 48 is arranged to interconnect with the chamber 90.

The process of inspecting the turbine blade 86 is the same as that described with reference to FIG. 4, however the steam flows through the film cooling passages 92 as a plurality of impingement jets which impinge upon the first, inner, surface 83 of the vessel 84. The camera 56 is arranged to view the second, outer, surface 85 of the vessel 84, to detect transient hot spots on the outer surface 85 of the vessel 84.

Figure 8:
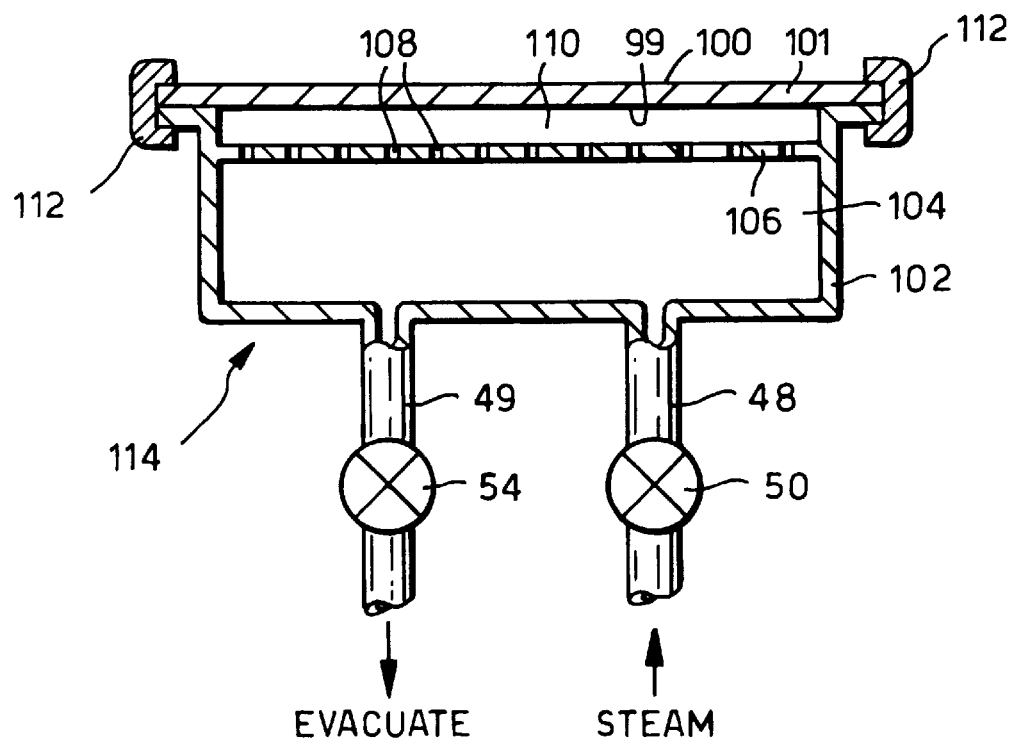
FIG. 8 is a further apparatus for inspecting an article according to the present invention.

An apparatus 114 for inspecting an article 100 is shown in FIG. 8. The apparatus 114 is substantially the same as the apparatus 42 but differs because the article 100 is not a turbine blade, is not hollow and does not have film cooling passages extending through the article 100.

The apparatus 114 differs in that a vessel 102 is placed over the article 100. The interior of the vessel 102 is divided into a first chamber 104 and a second chamber 110 by a plate 106. The plate 106 is spaced from the article 100 by a uniform clearance 110 to define the second chamber 110 between the plate 106 and the article 100. The open end of the vessel 114 is sealed to the article 100 by one or more clamps and/or seals 112. The plate 106 is provided with a plurality of passages 108 to direct jets of steam onto a first surface 99 of the article 100. The pipe 48 is arranged to interconnect with the first chamber 104 for the supply of steam to the first chamber 104. A pipe 49 is arranged to interconnect with the first chamber 104 for the evacuation of the first chamber 104. A camera is arranged to view the second surface 101 of the article 100.

The process of inspecting the article 100 is the same as that described with reference to FIG. 4, however the steam flows through the plurality of passages 108 as impingement jets which impinge upon the first surface 99 of the article 100. The camera is arranged to view the second surface 101 of the vessel 100 to detect transient hot spots on the second surface 101 of the article 100. The technique is used in this embodiment to detect variations in the thermal diffusivity in the article 100 and hence to detect defects in the article 100, for example voids, cracks, areas of corrosion or areas of oxidation. If the article is a composite or laminated material the technique may detect areas with debonds or delaminations. If the article has a coating the technique may detect areas with poor adhesion of the coating. The resolution may be achieved by increasing the number of passages 108 per unit area in the plate 106.

Although the invention has described the use of steam to inspect the articles, it is also possible to use any other suitable condensable heating fluid.

Although the invention has described the use of a vacuum pump to evacuate the articles, or enclosed volume, to remove gas, or air, from the article, or enclosed volume, it may be possible to remove the gas, or air, in other ways. For example ammonia, or other gas that is highly soluble in the condensable heating fluid, may be supplied to the enclosed volume to purge the gas, or air, from the enclosed volume. However, this is not preferred because it is necessary to provide an exit pipe and valve to allow the displaced gas, or air, out of the enclosed volume. Additionally there are problems of handling the ammonia and any waste product gases but the need for a vacuum pump would be removed.

Although the invention has referred mainly to turbine blades it is equally applicable to turbine vanes and other articles.

Although the invention has described the use of jets of steam directed to impinge upon the surface of the article or vessel to provide impingement heat transfer to the article or vessel, it may be possible to arrange for the steam to flow over the surface of the article if the surface of the article has other heat transferring features on its first, inner, surface such as ribs, strips, pedestals. These features will transfer heat into the wall of the turbine blade to create hot spots on the second, outer, surface of the aerofoil portion of the turbine blade.

I claim:

1. A method of inspecting an article, the article having a first surface and a second surface facing in the opposite direction to the first surface, comprising the steps of:
   (a) forming an enclosed volume at least partially fined by the first surface of the article,
   (b) removing gas from the enclosed volume,
   (c) supplying a condensable heating fluid to the closed volume,
   (d) directing a flow of the condensable heating fluid onto or over the first surface of the article to cause the temperature of the first surface to change,
   (e) viewing the second surface of the article during the temperature change to produce a series of images, and
   (f) analysing the series of images to determine the presence or absence of defects in the article.

2. A method as claimed in claim 1 wherein the method comprises injecting a small quantity of the condensable heating fluid into the enclosed volume after step (a) and before step (b).

3. A method as claimed in claim 1 wherein the method comprises injecting a small quantity of the condensed heating fluid into the enclosed volume after step (a) and before step (b).

4. A method as claimed in claim 1 wherein step (c) comprises supplying steam to the enclosed volume.

5. A method as claimed in claim 1 wherein step (e) comprises applying a thermochromic material to the second surface of the article and viewing the second surface of the article with a camera sensitive to radiation in the visible light band.

6. A method as claimed in claim 5 wherein step (e) comprises viewing the second surface of the article with camera selected from the group comprising a video camera, cine camera and a CCD camera.

7. A method as claimed in claim 1 wherein step (e) comprises viewing the second surface of the article with a camera sensitive to radiation in the infra red band.

8. A method as claimed in claim 7 comprising applying a calibrated emissivity coating to the second surface of the article.

9. A method as claimed in claim 1 wherein step (d) comprises directing a plurality of jets of the condensable heating fluid onto the first surface of the article.

10. A method as claimed in claim 1 wherein step (a) comprises forming the enclosed volume solely by the first surface of the article.

11. A method as claimed in claim 10 wherein step (d) comprises directing a plurality of jets of the condensable heating fluid through passages in the article onto the first surface of the article.

12. A method as claimed in claim 1 wherein the article is selected from the group comprising a turbine blade or a turbine vane.

13. A method as claimed in claim 1 wherein step (a) comprises forming the enclosed volume partially with a vessel.

14. A method as claimed in claim 13 wherein step (d) comprises supplying a plurality of jets of the condensable heating fluid through passages in the vessel onto the first surface of the article.

15. A method as claimed in claim 14 wherein the article is selected from the group comprising composite material article, a laminated material article and a coated article.

16. A method as claimed in claim 1 wherein step (b) comprises evacuating the enclosed volume.

17. A method of inspecting an article, the article having a plurality of passages extending from a first surface to a second surface facing in the opposite direction to the first surface, comprising the steps of:

(a) forming an enclosed volume at least partially defined by the second surface of the article and a first surface of a vessel, (b) removing gas from the enclosed volume, (c) supplying a condensable heating fluid to the enclosed volume, (d) directing a flow of the condensable heating fluid through the passages onto the first surface of the vessel to cause the temperature of the first surface of the vessel to change, (e) viewing the second surface of the vessel during the temperature change to produce a series of images, and (f) analysing the series of images to determine the presence or absence of defects in the article.

18. A method as claimed in claim 17 wherein the method comprises injecting a small quantity of the condensable heating fluid into the enclosed volume after step (a) and before step (b).

19. A method as claimed in claim 17 wherein the method comprises injecting a small quantity of the condensed heating fluid into the enclosed volume after step (a) and before step (b).

20. A method as claimed in claim 17 wherein step (c) comprises supplying steam to the enclosed volume.

21. A method as claimed in claim 17 wherein step (e) comprises applying a thermochromic material to the second surface of the article and viewing the second surface of the vessel with a camera sensitive to radiation in the visible light band.

22. A method as claimed in claim 21 wherein step (e) comprises viewing the second surface of the vessel with a video camera, a cine camera or a CCD camera.

23. A method as claimed in claim 17 wherein step (e) comprises viewing the second surface of the vessel with a camera sensitive to radiation in the infra red band.

24. A method as claimed in claim 23 comprising applying a calibrated emissivity coating to the second surface of the vessel.

25. A method as claimed in claim 17 wherein step (d) comprises directing a plurality of jets of the condensable heating fluid onto the first surface of the vessel.

26. A method as claimed in claim 17 wherein step (d) comprises directing a plurality of jets of the condensable heating fluid through passages in the article onto the first surface of the vessel.

27. A method as claimed in claim 17 wherein the article is selected from the group comprising a turbine blade and a turbine vane.

28. A method as claimed in claim 17 wherein step (b) comprises evacuating the enclosed volume.

29. An apparatus for inspecting an article, the article having a first surface and a second surface facing in the opposite direction to the first surface, the first surface at least partially defining an enclosed volume, comprising means to remove gas from the enclosed volume, means to supply a condensable heating fluid to the enclosed volume, means to direct a flow of the condensable heating fluid onto or over the first surface of the article to cause the temperature of the first surface to change, means to view the second surface of the article during the temperature change to produce a series of images, and means to analyse the series of images to determine the presence or absence of defects in the article.

30. An apparatus as claimed in claim 29 comprising means to inject a small quantity of the condensed heating fluid into the enclosed volume.

31. An apparatus as claimed in claim 29 wherein the means to supply a condensable heating fluid comprises a supply of steam.

32. An apparatus as claimed in claim 29 wherein the second surface of the article, has a thermochromic material.

33. An apparatus as claimed in claim 32 wherein the means to view the second surface of the article, comprises a camera sensitive to radiation in the visible light band.

34. An apparatus as claimed in claim 33 wherein the means to view the second surface of the article is selected from the group comprising a video camera, a cine camera and a CCD camera.

35. An apparatus as claimed in claim 29 wherein the means to view the second surface of the article comprises a camera sensitive to radiation in the infra red band.

36. An apparatus as claimed in claim 35 wherein the second surface of the article has a calibrated emissivity coating.

37. An apparatus as claimed in claim 29 wherein the enclosed volume is defined solely by the first surface of the article.

38. An apparatus as claimed in claim 37 wherein the article comprises a plurality of passages to direct a plurality of jets of the condensable heating fluid onto the first surface of the article.

39. An apparatus as claimed in claim 29 wherein the article is selected from the group comprising a turbine blade and a turbine vane.

40. An apparatus as claimed in claim 39 wherein the article is selected from the group comprising a composite material article, a laminated material article and a coated article.

41. An apparatus as claimed in claim 29 wherein the enclosed volume is defined by the first surface of the article and a first surface of a vessel.

42. An apparatus as claimed in claim 29 wherein the means to remove gas from the enclosed volume comprises a vacuum pump.

43. An apparatus for inspecting an article, the article having a plurality of passages extending from a first surface to a second surface facing in the opposite direction to the first surface, comprising a vessel having a first surface to define an enclosed volume with the second surface of the article, means to remove gas from the enclosed volume, means to supply a condensable heating fluid to the enclosed volume, means to direct a flow of the condensable heating fluid onto or over the first surface of the vessel to cause the temperature of the first surface to change, means to view the second surface of the article during the temperature change to produce a series of images, and means to analyse the series of images to determine the presence or absence of defects in the article.

44. An apparatus as claimed in claim 43 wherein the article comprises a plurality of passages to direct a plurality of jets of the condensable heating fluid onto the first surface of the vessel.

45. An apparatus as claimed in claim 43 wherein the vessel comprises a plurality of passages to direct a plurality of jets of the condensable heating fluid onto the first surface of the article.

46. An apparatus as claimed in claim 43 wherein the means to remove gas from the enclosed volume comprises a vacuum pump.

* * * * *